April 25, 1961 L. A. DEAN Plant Pat. 2,053
ROSE PLANT
Filed June 28, 1960
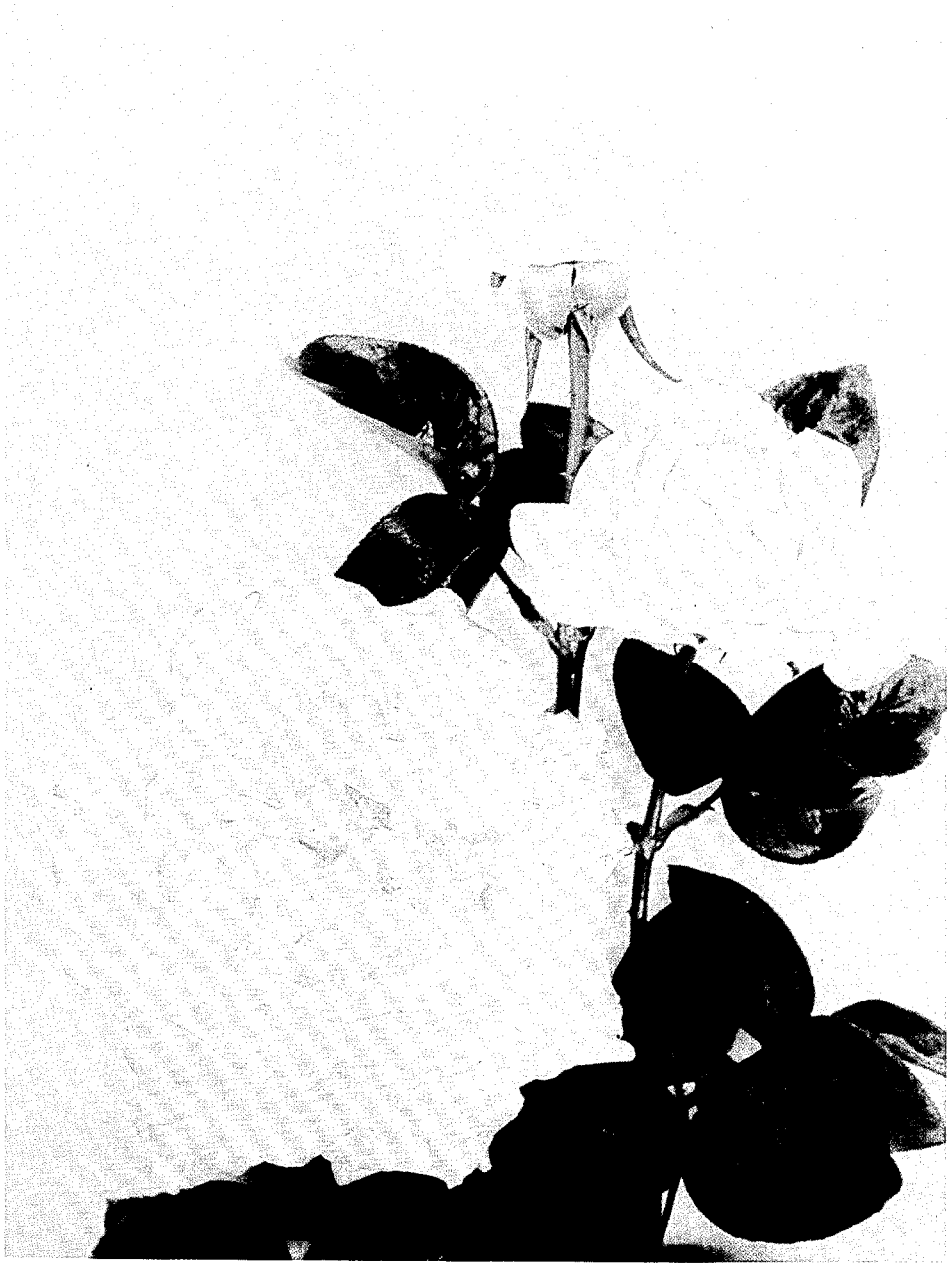
INVENTOR
L. A. Dean
BY Robert Cobb
ATTORNEYS United States Patent Office Plant Pat. 2,053
Patented Apr. 25, 1961

2,053

ROSE PLANT

Letcher A. Dean, Tyler, Tex., assignor, by mesne assignments, to The Conard-Pyle Company, West Grove, Pa., a corporation of Pennsylvania Filed June 28, 1960, Ser. No. 39,419

1 Claim. (Cl. 47—61)

The present invention relates to a new and distinct variety of rose plant of the hybrid tea class, which was discovered by me as a bud sport of the variety "Peace" (Plant Patent No. 591).

This new rose variety was discovered by me amongst a field of "Peace" roses that were being grown under my direction and control in the nursery fields of my assignee, at Arp, Texas. At the time of this discovery, my attention was attracted to one plant in the field of "Peace" roses aforesaid by virtue of the fact that it bore flowers of a color substantially different from the normal color of the flowers of "Peace." This difference in flower color was evidenced by a very different placement of the red coloration, with the red coloring having the form of a distinct picotee-like margin or border ranging from Spinel Red to Neyron Rose, as distinguished from the Martius Yellow general coloration of the flowers of "Peace," with the latter usually showing some diffuse rose pink markings.

Upon close examination of this plant, I found that it had sported and I thereupon took steps to preserve the sport, keep it under observation, and to later asexually reproduce the same. My observations and asexual reproductions as performed by budding at Arp, Texas, and also at West Grove, Pennsylvania, fully confirmed the new flower color characteristics of the sport and conclusively established that these characteristics come true to form and are transmissible through succeeding propagations.

Other than the specific differences in the flower color, as noted in the foregoing, the new sport is substantially identical to the parent variety "Peace" and, accordingly, it is unnecessary to completely describe the new sport, since the features other than the flower color are substantially the same as described and illustrated in Plant Patent No. 591, granted June 15, 1943, to which reference may be readily had.

There are two other patented sports of the variety "Peace" with which I am familiar and which vary from this parent substantially only with respect to the flower color. Of these previous sports, just referred to, the variety which is the subject of Plant Patent No. 1,282 is characterized by pink flowers which have a white border on the flower petals, while the flowers of my new variety are essentially Primrose Yellow in color with a heavy picotee margin of Spinel Red.

In comparison with the other sport, referred to above, which is the subject of Plant Patent No. 1,750, and which is characterised by flowers of light pink general tonality, here again there is a substantial difference in the flowers of my new variety which are essentially Primrose Yellow, with a heavy picotee-type margin of Spinel Red.

The accompanying drawing shows typical specimens of the flowers and foliage of my new variety in different stages of development and as depicted in color as nearly true as is reasonably possible to make the same in a color illustration of this character.

For convenience, the following is a detailed description of the flowers of my new rose variety, from which the distinctions over those of the parent variety, as well as over all other varieties, will be apparent, with color nomenclature in accordance with the Horticultural Color Chart of the Royal Horticultural Society:

*Flower*

Locality where grown and observed: Arp, Texas, and West Grove, Pennsylvania.

Bud:

*As calyx breaks.*—Color—Citron Green, Plate 763/2, lined with Crimson, Plate 22.

*As first petal opens.*—Color: Outside—Primrose Yellow, Plate 601/1, overlaid with Erythrite Red, Plate 0027/1 where first exposed to light, and irregularly washed with Spinel Pink, Plate 0625/3; Inside—Primrose Yellow, Plate 601 at base of petal, grading to Primrose Yellow, Plate 601/2, and with margin of petal Spinel Red, Plate 0023/1.

This description of a newly opened flower was made from a rose grown in the month of July at West Grove, Pennsylvania:

*Color.*—Outer petal: outside surface—Rhodonite Red, Plate 0022, bordering Carmine Rose, Plate 621/3 over apical half of petal; basal half of petal Primrose Yellow, Plate 601/3, with point of attachment Primrose Yellow, Plate 601/1; inside surface—main body of petal Primrose Yellow, Plate 601/2, heavily margined with Spinel Red, Plate 0023/1 with base of petal Primrose Yellow, Plate 601. Intermediate petal: outside surface—Dawn Pink, Plate 523/3 at apical margin, grading to Naples Yellow, Plate 403/3 and then to Primrose Yellow, Plate 601/3, with point of attachment Primrose Yellow, Plate 601/1; inside surface—Primrose Yellow, Plate 601/3, margined with Neyron Rose, Plate 623/2 and grading to Primrose Yellow, Plate 601 at point of attachment. Inner petal: outside surface—Primrose Yellow, Plate 601/3, with point of attachment Primrose Yellow, Plate 601/1; inside surface—main body of petal Primrose Yellow, Plate 601/3, streaked and washed with Rhodonite Red, Plate 0022/3, with point of attachment Primrose Yellow, Plate 601.

This description was made from a rose that was open for 3 days in the month of July at West Grove, Pennsylvania:

*Color.*—Outer petal: outside surface—Primrose Yellow, Plate 601/3, lightly overcast with Empire Rose, Plate 0621/3; inside surface — between Tyrian Rose, Plate 24/2 and Tyrian Rose, Plate 24/3 where exposed to sun, with remainder of petal Primrose Yellow, Plate 601/3.

Inner petal: Outside surface — Primrose Yellow, Plate 601/3, washed and specked with Empire Rose, Plate 0621/3; inside surface—between Tyrian Rose, Plate 24/2 and Tyrian Rose, Plate 24/3 over upper half of petal, becoming Primrose Yellow, Plate 601/3 specked with Tyrian Rose, Plate 24/2 and then Primrose Yellow, Plate 601/3.

*General color effect.*—Newly opened flower—Primrose Yellow, Plate 601/3, heavily margined with Spinel Red, Plate 0023/1. 3 days open—Primrose Yellow, Plate 601/3, with upper half of petal Tyrian Rose, Plate 24/2.

I claim:

A new and distinct variety of rose plant of the hybrid tea class, substantially as herein shown and described, characterized particularly as to novelty by being generally similar to its parent variety "Peace" (Plant Patent No. 591), but being distinguished therefrom by a Primrose Yellow general color tonality of the flower petals and their picotee-like margins ranging in color from Spinel Red to Neyron Rose.

No references cited.